United States Patent
Gu et al.

(10) Patent No.: US 10,526,370 B2
(45) Date of Patent: Jan. 7, 2020

(54) PENTAPEPTIDE ASSOCIATED WITH INTEGRIN RECEPTOR ALPHA VBETA3

(71) Applicant: CHINA PHARMACEUTICAL UNIVERSITY, Nanjing, Jiangsu (CN)

(72) Inventors: Yueqing Gu, Nanjing (CN); Congying Zhang, Nanjing (CN); Menglu Zhao, Nanjing (CN); Qian Wang, Nanjing (CN); Caiping Tian, Nanjing (CN); Yuxi Liu, Nanjing (CN)

(73) Assignee: CHINA PHARMACEUTICAL UNIVERSITY, Nanjing, Jiangsu (CN)

( * ) Notice: Subject to any disclaimer, the term of this patent is extended or adjusted under 35 U.S.C. 154(b) by 0 days.

(21) Appl. No.: 15/568,315

(22) PCT Filed: Oct. 26, 2015

(86) PCT No.: PCT/CN2015/092827
§ 371 (c)(1),
(2) Date: Oct. 20, 2017

(87) PCT Pub. No.: WO2016/169239
PCT Pub. Date: Oct. 27, 2016

(65) Prior Publication Data
US 2018/0141974 A1 May 24, 2018

(30) Foreign Application Priority Data

Apr. 20, 2015 (CN) .......................... 2015 1 0190462

(51) Int. Cl.
*G01N 33/53* (2006.01)
*C07K 5/00* (2006.01)
*C07K 7/06* (2006.01)
*A61P 35/00* (2006.01)
*G01N 33/574* (2006.01)

(52) U.S. Cl.
CPC ................ *C07K 7/06* (2013.01); *A61P 35/00* (2018.01); *G01N 33/574* (2013.01)

(58) Field of Classification Search
None
See application file for complete search history.

(56) References Cited

U.S. PATENT DOCUMENTS

| 6,610,836 B1 * | 8/2003 | Breton ................... C07K 14/26 435/320.1 |
| 2007/0044171 A1 * | 2/2007 | Kovalic .................. A01G 22/00 800/278 |

FOREIGN PATENT DOCUMENTS

| CN | 101497656 A | 8/2009 |
| CN | 103044522 A | 4/2013 |
| CN | 104774247 A | 7/2015 |
| WO | 2008/088548 A2 | 7/2008 |

OTHER PUBLICATIONS

UniProtKB—W1XBT3 (W1XBT3_ECOLX). Cytochrome d ubiquinol oxidase subunit 2. (Mar. 19, 2014) (Year: 2014).*
Lee et al., "High-Throughput Screening of Novel Peptide Inhibitors of an Integrin Receptor from the Hexapeptide Library by Using a Protein Microarray Chip," Journal of Biomolecular Screening, 2004, vol. 9, No. 8, pp. 687-694.
Jan. 18, 2016 International Search Report issued in International Patent Application No. PCT/CN2015/092827.

* cited by examiner

Primary Examiner — Maher M Haddad
(74) Attorney, Agent, or Firm — Oliff PLC

(57) ABSTRACT

A pentapeptide associated with integrin receptor αvβ3, which has a sequence of arginine-tryptophan-arginine-asparagine-methionine. The pentapeptide targets tumor cells highly expressing αvβ3, but not tumor cells lowly expressing αvβ3 and normal cells. Accordingly, the pentapeptide is useful in the diagnosis and treatment of cancers.

7 Claims, 6 Drawing Sheets
Specification includes a Sequence Listing.

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial
<220> FEATURE:
<223> OTHER INFORMATION: Synthetic peptide

<400> SEQUENCE: 1

Arg Trp Arg Asn Met
1               5
```

PENTAPEPTIDE ASSOCIATED WITH INTEGRIN RECEPTOR ALPHA VBETA3

BACKGROUND

Technical Field

The present invention relates to the technical field of biopharmaceutics, protein and peptide drugs, and biomedical engineering, and specifically to a pentapeptide associated with integrin receptor alpha vbeta3 (αvβ3).

Related Art

Currently, cancers are one of the leading causes of death in human beings, and the chemotherapy is still a major method for cancer treatment. However, because traditional chemotherapeutic agents are not specific for tumor cells, some organ toxicities occur in patients.

Integrins are widely expressed in cells. Most of the cells can express more than one integrins on their surfaces. Such integrins are not only involved in the physiological functions of some cells such as growth, division and apoptosis, but also play an important role in various pathological processes. The integrin family includes 18 α subunits and 8 β subunits, and the pairing between the α and β subunits determines the ligand specificity. In the integrin superfamily, the integrin receptor αvβ3 plays a critical role in imaging and targeted therapy. Due to the high expression of the integrin receptor αvβ3 in many tumors, such as glioma, breast cancer, melanoma, prostate cancer and ovarian cancer, the integrin receptor αvβ3 becomes an important drug target. At present, the tripeptide having a sequence of arginine-tryptophan-arginine has been shown to be a polypeptide with a high affinity for integrin αvβ3 (for more details, see Patent Application No. 201310019870.9, entitled "Polypeptide Having High Affinity For Integrin Receptor αvβ3").

SUMMARY

An object of the present invention is to provide a polypeptide targeting the integrin receptor αvβ3, making it possible to diagnose the tumors highly expressing the integrin receptor αvβ3.

A polypeptide with a high affinity for the integrin receptor αvβ3 is provided, which has a sequence of Arg-Trp-Arg-Asn-Met (SEQ ID NO: 1).

Use of the polypeptide of the present invention in the preparation of tumor diagnostics is further provided.

The tumor is preferably a tumor highly expressing the integrin receptor αvβ3, and further preferably glioma, breast cancer, melanoma, prostate cancer and ovarian cancer.

Use of the polypeptide of the present invention in the preparation of medicines for treating tumors is further provided.

The tumor is preferably a tumor highly expressing the integrin receptor αvβ3, and further preferably glioma, breast cancer, melanoma, prostate cancer and ovarian cancer.

Beneficial Effect:

To detect the affinity of the polypeptide of the present invention for tumor cells highly expressing the integrin receptor, the polypeptide is labeled with the fluorescent dye rhodamine B in an in vitro experiment to detect the targeting of the peptide against tumors. In an in vitro cell affinity assay and a cellular uptake assay, the pentapeptide of the present invention is shown to target the integrin receptor αvβ3 in tumor cells much more potently than the tripeptide. In an in vitro cellular cytotoxicity assay, the pentapeptide of the present invention exhibits a low cytotoxicity, and is particularly useful in the development of diagnostics for integrin receptors.

In the figure, Curve A represents RWrNM-RhB, Curve B represents cRGD-RhB, Curve C represents RWr-RhB, Curve D represents RGD-RhB, Curve E represents RhB, and Curve F represents cells exclusively.

Figure 2:
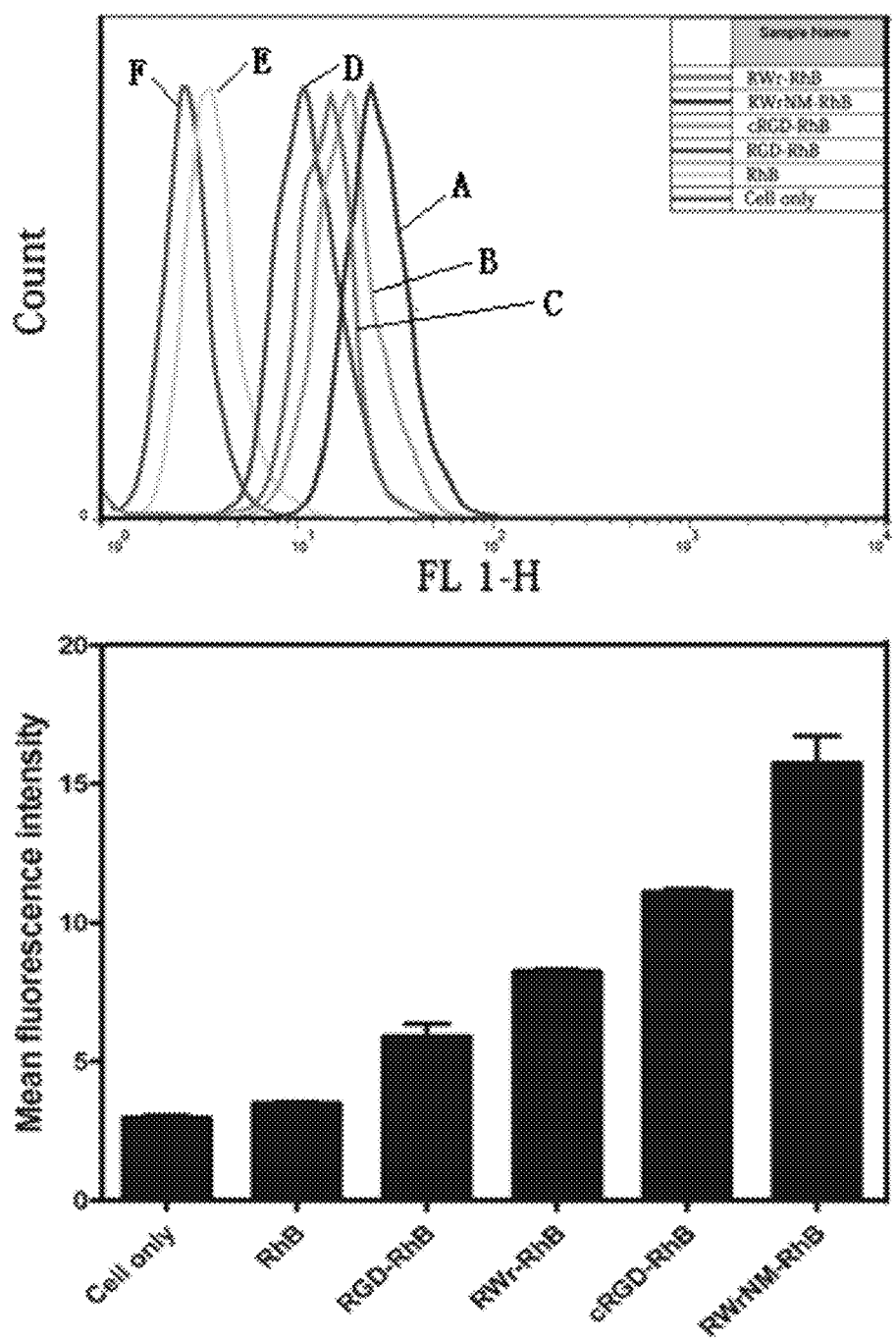

FIG. 2 shows the affinity of various peptides (labeled with rhodamine) for MDA-MB-231 cells.

In the figure, Curve A represents RWrNM-RhB, Curve B represents cRGD-RhB, Curve C represents RWr-RhB, Curve D represents RGD-RhB, Curve E represents RhB, and Curve F represents cells exclusively.

The result of flow cytometry reveals that the affinities of these peptides are ranked in the order: A>B>C>D>E, indicating that the new combined peptide RWrW has a affinity for both cells greater than that of cyclic RGDyk, and significantly greater than that of the tripeptide RWr. The linear RGD has the weakest affinity among those peptides.

Figure 3:
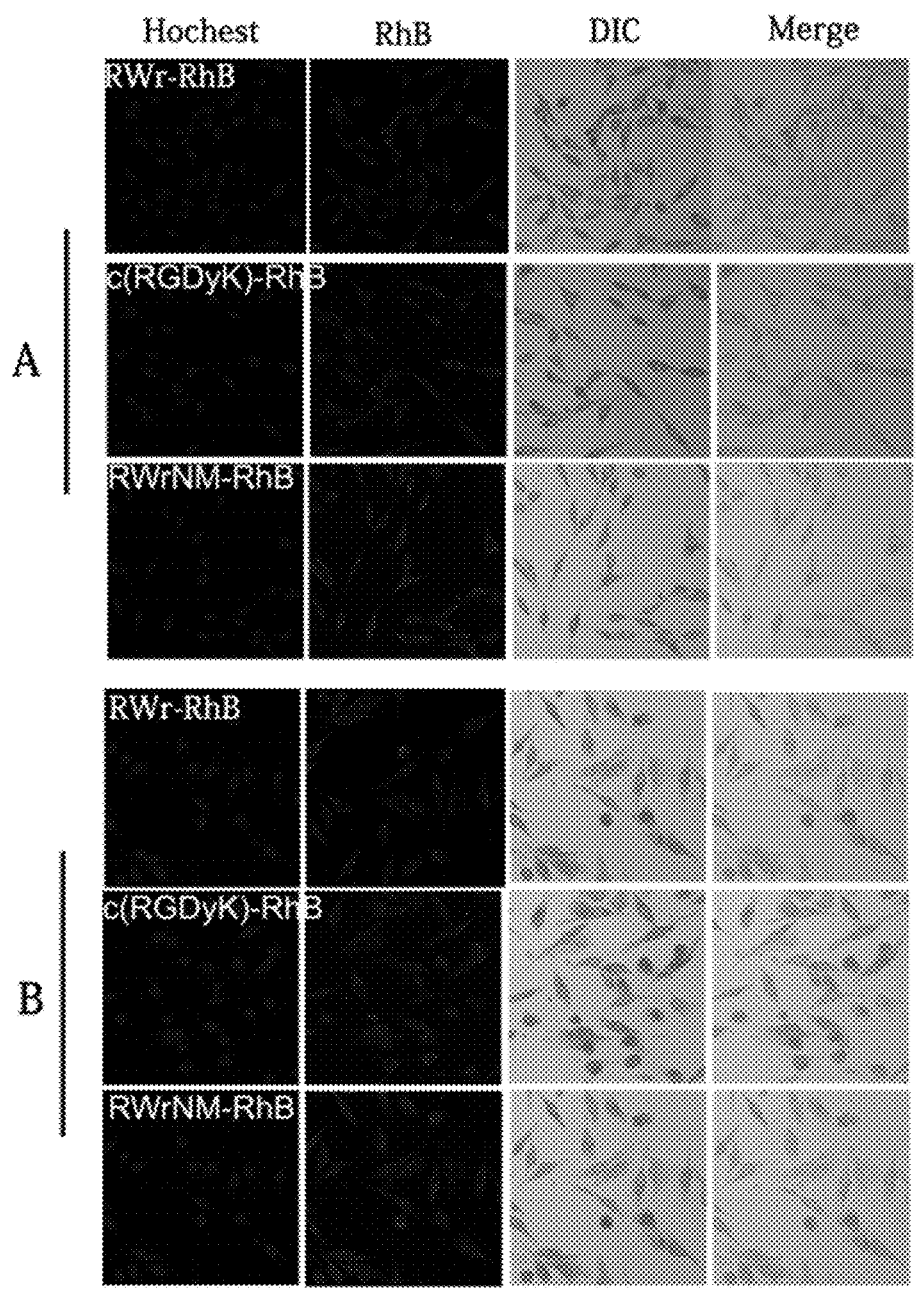

FIG. 3 shows the observations by laser confocal microscopy of the uptake of rhodamine B-labeled probes by various tumor cells in a cellular uptake assay (A represents U87MG cells, and B represents MDA-MB-231 cells).

Figure 4:
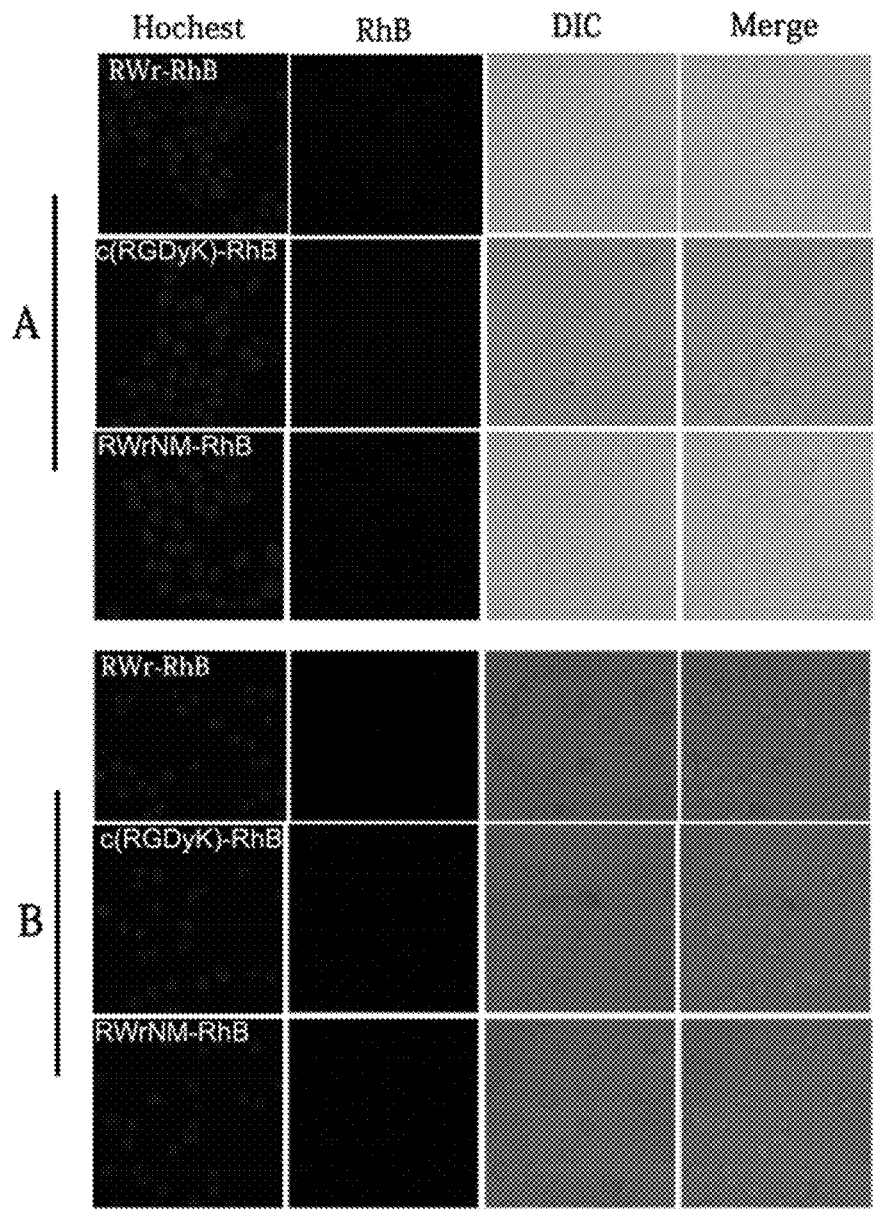

FIG. 4 shows the observations by laser confocal microscopy of the uptake of rhodamine B-labeled probes by various tumor cells in a cellular uptake assay (A represents MCF-7 cells, and B represents L02 cells).

The result shows that as can be seen from the figure, the cells highly expressing the integrin receptors, such as U87, and 231, have a strong ability to uptake the pentapeptide, and the cells lowly expressing the integrin receptors, such as MCF-7 and L02, have a poor affinity for the pentapeptide; however, the pentapeptide has a greater affinity for the cells than cRGD and Rwr.

Figure 5:
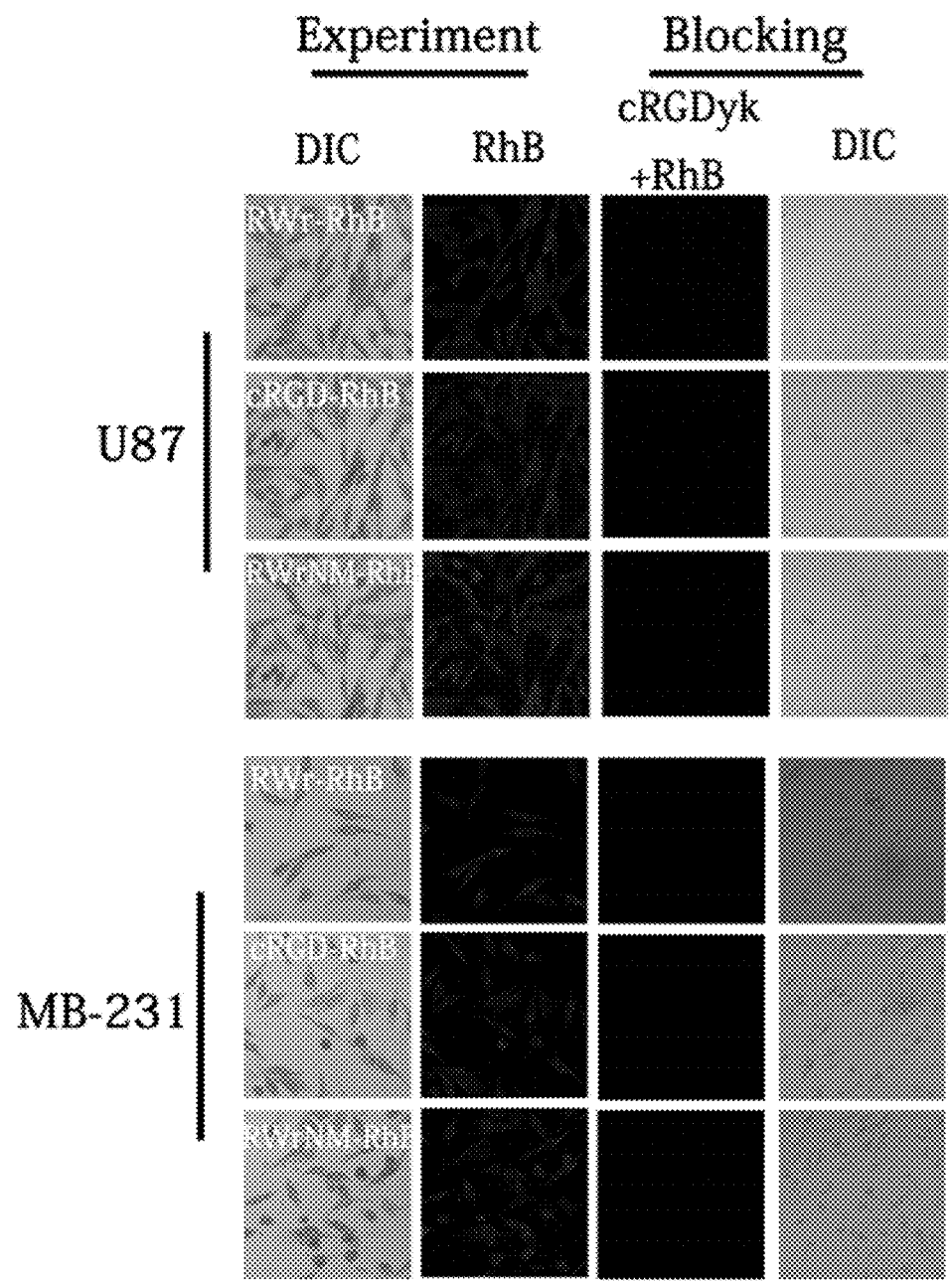

FIG. 5 shows the result of a competitive blocking assay.

The result shows that due to the competitive binding of cRGD and the integrin receptor αvβ3, the other small peptides cannot bind to the cells, indicating that the binding targets of these small peptides are αvβ3.

Figure 6:
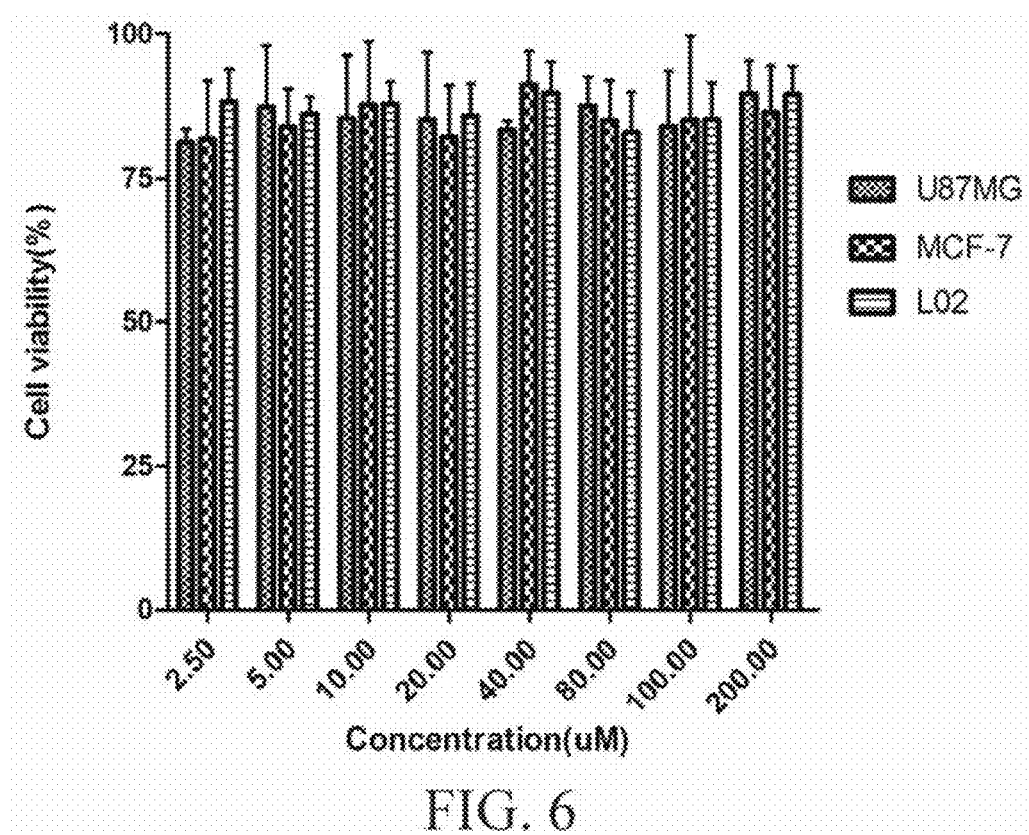

FIG. 6 shows the evaluation of the cytotoxicity of the pentapeptide to different cells in an in vitro cellular cytotoxicity assay. The pentapeptide is shown to have a low toxicity to those cells, and thus can be safely used as a diagnostic reagent.

DETAILED DESCRIPTION

Example 1

Synthesis of the Pentapeptide

1: Conjugation

Fmoc-Met-Rink amide MBHA resin (fluorenylmethoxycarbonyl-phenylalanine-rink amide resin; 0.33/2 mmol, 6.06 g) was swelled in dimethylformide in an amount of 10 ml/g resin, and then the Fmoc group was deprotected from the resin with 20% piperdine/dimethylformide solution (referred to as "decapped" below). The decapped resin was washed with dimethylformide, and the material Fmoc-Asn (tBU)-OH (2.3 g) was added. HBTU (1.44 g) was used as a condensing agent, and reacted for 30 min. A negative result as detected by Kaiser test indicated that the conjugation was complete, and then decapping was carried out for 30 min. A positive result indicated that the conjugation was not completed or incomplete. The conjugation time was increased or the materials were additionally added, until the conjugation was complete. These steps were repeated and Fmoc-D-Arg (Pbf)-OH, Fmoc-Trp-OH, and Fmoc-Arg(Pbf)-OH were sequentially conjugated. After the synthesis of the linear peptides, the resulting peptidyl resin was washed with methanol, and fully dried in a vacuum oven.

2: Separation and Cleavage of the Peptide from the Resin 120 ml cleavage cocktail (10 ml/g peptidyl resin) was added to the resin. The mixture was magnetically stirred at 25° C. for 2.5 h. The cleavage cocktail was separated from the resin by using a filter funnel with fritted disc. The resin was discarded, and the filtrate was collected. The filtrate was slowly added dropwise to 10 volume equivalents of ice-cold dry diethyl ether. After the addition was complete, the system was left to settle for 30 min. Then, the system was centrifuged with a high-speed centrifuge for 10 min (at 4000 rpm). The supernatant was discarded, and the precipitate was collected. The resulting precipitate was dried in an oven for 8-10 h to provide a crude dry powder.

3: Purification

The crude dry powder described above (1 g) was dissolved in 0.1% trifluoroacetic acid/water. After filtration, it was loaded on a C18 Preparative column, and purified by high performance liquid chromatography with gradient elution. The fraction containing target peptide was collected, and the purity of the liquid was determined. The samples having defined purities were combined, and then evaporated on a rotary evaporator. Finally, it was lyophilized in a lyophilizer to obtain Arg-Trp-Arg-Asn-Met (SEQ ID NO: 1) (purity >98%).

Sequence: Arg-Trp-Arg-Asn-Met (SEQ ID NO: 1).

It can be seen in the mass spectrum that Arg-Trp-Arg-Asn-Met (SEQ ID NO: 1) has a molecular weight of 381.7*2−2=761.4.

An absorption peak of the peptide can be seen at 273 nm in the UV spectrum.

Example 2

1. Labeling with an Fluorescent Dye

The fluorescent dye used in an in vitro cellular experiment of the present invention was rhodamine B, or RhB for short. RhB was linked to the tripeptide described above and the pentapeptide of the present invention via an amide bond respectively, which was termed as RWr-RhB and RWrNM-RhB respectively for short. The linking process was specifically as follows. 1 mg rhodamine B (for more details, see reference: Cao, J., et al., *Fast clearing RGD-based near-infrared fluorescent probes for in vivo tumor diagnosis.* Contrast Media Mol Imaging, 2012. 7(4): p. 390-402) was dissolved in 1 ml PBS (pH 7.4). 1-ethyl-(3-dimethylaminopropyl)carbodiimide hydrochloride, and N-hydroxysuccinimide (EDC/NHS) (molar ratio Rhodamine B:EDC:NHS=1: 1.5:1.5) were added, and reacted in the dark for 4 h for activation. Each 1 mmol of the tripeptide and the pentapeptide was dissolved in 1 ml PBS buffer (pH 7.4) containing the fluorescent dye rhodamine B, and the mixture was stirred overnight in the dark at room temperature. After the reaction was complete, the reaction solution was concentrated, and then passed through a Sephadex G-25 column eluting with a PBS buffer (pH 7.4), to afford purified RWr-RhB and RWrNM-RhB, which were stored at −20° C. for later use. The cyclic RGD was also labeled through the same method and used as a control, which was referred to as c(RGDyK)-RhB for short.

2. In Vitro Cell Affinity Test

Figure 1:
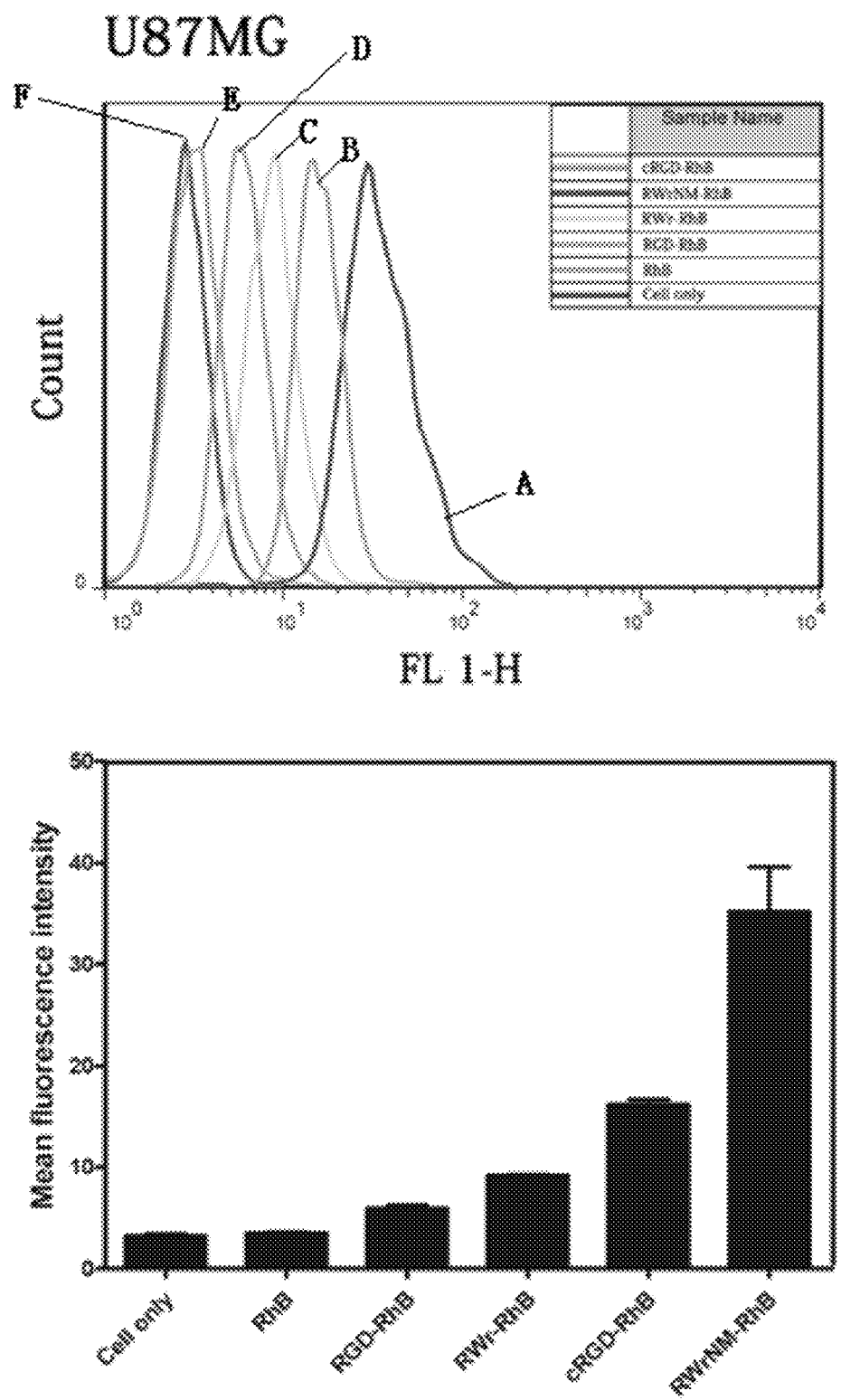
FIG. 1 shows the affinity of various peptides (labeled with rhodamine) for U87 cells.

The human malignant glioma cells (U87MG) and the human breast cancer cells (MDA-MB-231) were cultured in a 6-well plate for 12 hours. Then, 100 μL of a polypeptide fluorescent probe labeled with rhodamine B (final concentration 250 μM) was added and co-incubated for 2 hours with gently shaking on a shaker at 37° C. Next, the cells were digested with 0.05% trypsin and washed off from the 6-wells plate. The cells were re-suspended in 1 mL PBS buffer (pH 7.2), and centrifuged (3500 r, 5 min). The supernatant was aspirated and discarded. The pellet was washed twice with a PBS buffer (pH7.2). After washing, the cells were re-suspended in a PBS buffer (pH 7.2). The mean fluorescence intensity (MFI) of the cells was quantified by using a flow cytometer. The higher the fluorescence intensity is, the greater the affinity for the cells will be. When the probe has a high affinity for the receptor on the cells, the cells have a high value of MFI measured by the flow cytometer. As illustrated in FIGS. 1 and 2, the result of the in vitro affinity test shows that after the tripeptide and the pentapeptide probes labeled with RhB are respectively incubated at the same concentration with U87MG cells highly expressing the integrin receptor, the tripeptide probe has a MFI of 98 in U87MG cells, and the pentapeptide probe has a MFI of 123. The dye used as a blank has a MFI of 25. The affinities of these probes for the U87MG cells are compared and the result indicates that the pentapeptide of the present invention has the greatest affinity which is substantially higher than that of the tripeptide.

3. In Vitro Cellular Uptake Assay

The cultured human glioma cells U87MG, human breast cancer cells MDA-MB-231, human breast cancer cells MCF-7 and normal liver cells L02 were transferred to a confocal dish respectively, and incubated overnight. Then, the rhodamine B-labeled pentapeptide was added at the same concentration (500 μmol/L). The cyclic RGD labeled with the rhodamine B is added and used as a positive control. After 2-hour incubation at 37° C., the cells were stained with 12 μg/mL of the nuclear staining reagent Hochest 33342. Finally, the intracellular uptake of the probe was observed under a laser confocal microscope. In U87MG and MDA-MB-231 cells highly express the integrin receptor αvβ3 (as shown in FIG. 3), the cyclic RGD and the pentapeptide probes have a strong fluorescence intensity, and in MCF-7 and L02 cells lowly expressing the integrin receptor αvβ3 (as shown in FIG. 4), the fluorescence intensity of the two probes is low, suggesting that the pentapeptide probe can selectively target the cells which highly express the integrin receptor αvβ3 over the cells which lowly express the integrin receptor αvβ3.

4. In Vitro Competitive Binding Assay

To further demonstrate that the polypeptide specifically targets the cells which express the integrin receptor, a competitive blocking assay was adopted. An in vitro receptor blocking test was carried out. Specially, U87MG and MDA-MB-231 cell lines were respectively incubated in a confocal dish for 12 hours. Then, 0.1 mmol/L of the cyclic RGD was added, and incubated for an additional 30 min. Each 100 nmol/L of the probe solutions was added and the mixture was incubated for 2 hrs. The medium was removed and then the cells were washed three times with a PBS solution (pH 7.2). Then, the intracellular uptake of the probes was observed under a confocal microscope. As shown in FIG. 5, the fluorescence intensity of the tumor cells is substantially reduced, suggesting that the unlabeled cyclic RGD can competitively block the binding of both polypeptide probes to U87MG cells or MDA-MB-231 cells having a high expression of integrin. Additionally, it is further demonstrated that the pentapeptide can specifically bind to the integrin receptor on cell membrane in vitro.

5. In Vitro Cellular Cytotoxicity Assay

When the U87MG cells, MCF-7 cells and normal liver cells L02 were grown to 90% confluent or higher, the cells were digested with 0.25% trypsin and then suspended in a complete growth medium to obtain a single cell suspension. The cells were plated at a density of 3000 cells/well in a 96-well plate, and cultured at 37° C. in an incubator containing 5% $CO_2$. After 24-hour incubation, the medium was changed to a low-serum culture medium supplemented with 1% FBS. Then, the pentapeptide was added at different concentration gradients, to achieve a final concentration of 2.5, 5, 10, 20, 40, 80, 100 and 200 μM. As shown in FIG. 6, the result shows that the cell survival rate is 80% or higher in the presence of the pentapeptide, indicating that the pentapeptide is substantially non-toxic to these cells.

Taken together, the pentapeptide of the present invention can target the cells having a high expression of the integrin receptor αvβ3, but substantially not the cells having a low expression of the integrin receptor αvβ3; and the pentapeptide is substantially non-toxic to these cells. It can be seen that the pentapeptide can be used to diagnose the tumors which highly express the integrin receptor αvβ3 in vitro.

The pentapeptide of this example is prepared through solid-phase synthesis of Example 1.

---

---

What is claimed is:

1. A pentapeptide consisting of the amino acid sequence of SEQ ID NO: 1 attached to a dye or a medicine for treating tumors.

2. The pentapeptide of claim 1 labeled with a fluorescent dye.

3. The pentapeptide of claim 1 attached to a medicine for treating tumors.

4. A method of detecting cells expressing integrin αvβ3, the method comprising:
    binding the pentapeptide of claim 1 to the cells expressing integrin αvβ3.

5. The method according to claim 4, wherein the pentapeptide is labeled with a fluorescent dye.

6. The method according to claim 4, wherein the cell is a tumor cell.

7. The method according to claim 4, wherein the cell is a glioma, breast cancer, melanoma, prostate cancer, or ovarian cancer cell.

* * * * *